United States Patent
De Guise et al.

(10) Patent No.: US 9,286,355 B2
(45) Date of Patent: Mar. 15, 2016

(54) METHOD AND SYSTEM FOR HUMAN JOINT TREATMENT PLAN AND PERSONALIZED SURGERY PLANNING USING 3-D KINEMATICS, FUSION IMAGING AND SIMULATION

(71) Applicant: Emovi Inc., Laval (CA)

(72) Inventors: Jacques De Guise, Montreal (CA); Neila Mezghani, Montreal (CA); Alexandre Fuentes, Montreal (CA); Éric Szmutny, Philipsburg (CA); Guy Grimard, Ville Mont-Royal (CA); Pierre Ranger, Ste-Dorothée (CA); Nicola Hagemeister, Montreal (CA); Rachid Aissaoui, Montreal (CA); Thierry Cresson, Ottawa (CA); Julien Clément, Montreal (CA)

(*) Notice: Subject to any disclaimer, the term of this patent is extended or adjusted under 35 U.S.C. 154(b) by 229 days.

(21) Appl. No.: 13/743,057

(22) Filed: Jan. 16, 2013

(65) Prior Publication Data
US 2013/0185310 A1  Jul. 18, 2013

Related U.S. Application Data

(60) Provisional application No. 61/587,116, filed on Jan. 16, 2012.

(51) Int. Cl.
| | | |
|---|---|---|
| G06F 17/30 | (2006.01) | |
| G06F 17/50 | (2006.01) | |
| G06F 19/00 | (2011.01) | |

(52) U.S. Cl.
CPC ........ *G06F 17/3053* (2013.01); *G06F 17/5009* (2013.01); *G06F 19/321* (2013.01); *G06F 19/324* (2013.01); *G06F 19/3437* (2013.01)

(58) Field of Classification Search
CPC . G06F 17/50; G06F 17/5009; G06F 19/3437; G06F 19/3406; G06F 3/011; G06F 19/3443; G06F 19/3412; G06F 19/3431; G06F 19/324; G06F 17/3053; G06F 19/321; G06F 19/322
USPC .......................................................... 707/748
See application file for complete search history.

(56) References Cited

U.S. PATENT DOCUMENTS 5,533,519 A * 7/1996 Radke et al. ................... 600/595
7,291,119 B1 * 11/2007 de Guise et al. ............... 600/595
(Continued)

FOREIGN PATENT DOCUMENTS

WO 2011137515 11/2011

OTHER PUBLICATIONS

A Visualization Tool to convey Quantitative in vivo, 3D Knee Joint Kinematics, Seisler et al. Proceedings of the 35th Applied Imaginary and Pattern Recognition Workshop (AIPR'06).
(Continued)

*Primary Examiner* — Debbie Le
(74) *Attorney, Agent, or Firm* — Benoît & Côté Inc.

(57) ABSTRACT

The present document describes a method for producing a knee joint treatment plan and/or surgery plan for a patient, the method comprising: obtaining 3D kinematic data of the knee joint in movement; determining, from the 3D kinematic data, scores characterizing the joint function of the patient, the one or more scores being relative to one or more criteria; and comparing the scores to data in a database which characterize a plurality of treatment plans and/or surgery plans to generate the list of one or more treatment plans and/or surgery plans which match the scores.

20 Claims, 6 Drawing Sheets

(56) References Cited

U.S. PATENT DOCUMENTS

| | | | |
|---|---|---|---|
| 7,383,164 B2* | 6/2008 | Aram et al. | 703/7 |
| 8,036,729 B2 | 10/2011 | Lang et al. | |
| 8,260,593 B2* | 9/2012 | Raschke | 703/7 |
| 8,444,564 B2* | 5/2013 | Mahfouz et al. | 600/449 |
| 2003/0153978 A1* | 8/2003 | Whiteside | 623/20.21 |
| 2004/0167390 A1* | 8/2004 | Alexander et al. | 600/410 |
| 2009/0022382 A1* | 1/2009 | Feilkas et al. | 382/131 |
| 2010/0164862 A1* | 7/2010 | Sullivan et al. | 345/156 |
| 2012/0029345 A1* | 2/2012 | Mahfouz et al. | 600/427 |
| 2013/0177230 A1* | 7/2013 | Feng et al. | 382/132 |
| 2013/0211259 A1* | 8/2013 | Komistek et al. | 600/440 |

OTHER PUBLICATIONS

Automatic Classification of Asymptomatic and Osteoarthritis Knee Gait Patterns Using Kinematic data Features and the Nearest Neighbor Classifier. Mezghani et al., Mar. 2008, IEEE Transaction on Biomedical Engineering, vol. 55, No. 3., pp. 1230-1232.

Automatic Classification of Pathological Gait Patterns using Ground Reaction Forces and Machine Learning Algorithms, Alaqtash et al., Proceedings of the 33rd Annual International Conference of the IEEE EMBS, pp. 453-457. Aug. 30-Sep. 3, 2011, Boston, USA.

Gait Analysis Methods in Rehabilitation. Baker, Richard. Journal of NeuroEngineering and Rehabilitation. 3: Apr. 2006.

Knee Function Classification: An overview of the dempster-Shafer based ciassifer, Jones et al., Ninth Symposium on 3D Analysis of Human Movement, 2006 [retrieved on Mar. 13, 2013]. Retrieved from the internet: <URL: http://www.univ-valenciennes.fr/congres/3D2006/Abstracts/136-Jones.pdf.

PCT/International Search Report (ISR)—PCT/CA2013/000050 (Form PCT/ISA/210)—Apr. 2, 2013—7 pages.

Techniques for fusion of gait analysis with medical imaging data: exploitation in patients operated on massive skeletal reconstruction, Leardini et al., Ninth Symposium on 3D Analysis of Human Movement, 2006 [retrieved on Mar. 13, 2013]. Retrieved from the internet: <URL: http://www.univ-valenciennes.fr/congres/3D2006/Abstracts/125-Leardini.pdf>.

* cited by examiner

Flexion-Extension    Abduction-Adduction    Internal-External Rotation

METHOD AND SYSTEM FOR HUMAN JOINT TREATMENT PLAN AND PERSONALIZED SURGERY PLANNING USING 3-D KINEMATICS, FUSION IMAGING AND SIMULATION

CROSS-REFERENCE TO RELATED APPLICATIONS

This application claims priority from U.S. Application No. 61/587,116 dated Jan. 16, 2012.

BACKGROUND (a) Field

The subject matter disclosed generally relates to tools for planning surgery and or treatment. More specifically, the subject matter relates to such tools applied to the context of human joints.

(b) Related Prior Art

There exists a host of 3D knee biomechanical data which are precisely and repeatedly acquired by data acquisition system such as the KneeKG™ pre- and post-treatment.

Systems known in the arts dealing with surgery planning are based mostly on information obtained by reviewing medical imagery in static conditions and 3D simulation based on the static information. Systems known in the art may be radiography, magnetic resonance, CT Scans, KT-1000, specified clinical tests (i.e. pivot shift test and Lachman test) and the like. Current methods also involve the use of radiological examinations (such as X-rays, MRI, and CT-Scans). Such exams however remain limited in terms of their capacity to evaluate various functional aspects of the knee joint, and typically cannot be performed while the knee is moving (i.e. they are static in nature).

Other existing methods used for knee joint treatment planning for knee pathologies typically involve static imaging combined with manual testing (ligament laxity). Since these tests rely on manual testing and patient compliance, they are tainted by a certain amount of subjectivity.

Moreover, some existing methods permit quantification of anteroposterior movement of the tibia with respect to the femur (such as the KT-1000) in a knee joint treatment planning for knee pathologies. These methods however do not permit precise and reliable evaluation of the knee joint for a knee joint treatment planning for knee pathologies as they are typically limited to performing a static evaluation of a translation movement. Such methods are typically not suitable for performing an evaluation while a movement is being performed by the knee joint.

However, it is more and more recognized that the treatment must take into account the patient's mechanical articulation under dynamic and weight bearing conditions. A problem that therefore exists is the integration of these two types of information for various patients.

To this day, this problem is not yet resolved. Doctors do not integrate weight bearing 3D biomechanical information in the surgery treatment planning and when taking charge of a patient (for lack of tools). They only use 2D information and/or static information and make adjustments during surgery.

Major deficiencies are that many adjustments are required during the surgery. Doctors avoid this problem by applying generic techniques which are not optimal for all patients.

There is therefore a need for a method and for a system for knee joint treatment plan and personalized surgery planning and simulation using patient specific weight bearing kinematics with fusion of 3D imaging.

SUMMARY

There is described herein a system for knee joint treatment planning for knee pathologies (i.e.: osteoarthritis, patellofemoral pain syndrome, anterior cruciate ligament (ACL) lesion, meniscus lesion, tendonitis and the like) based on 3D kinematic data. The system uses 3D biomechanical data classification methods.

According to an embodiment, there is provided a method for generating a list of one or more joint treatment plans and/or surgery plans for a joint of a patient, the method comprising:
  obtaining, from motion sensors, 3D kinematic data of the joint in movement;
  determining, from the 3D kinematic data, scores characterising a joint function of the patient, the scores being relative to one or more criteria; and
  comparing the scores to data in a database which characterize a plurality of treatment plans and/or surgery plans to generate the list of one or more joint treatment plans and/or surgery plans which match the scores.

According to an aspect, the method further comprises simulating the one or more joint treatment plans and/or surgery plans using the 3D kinematic data to produce a plurality of modified 3D kinematic data.

According to an aspect, the method further comprises comparing the plurality of modified 3D kinematic data to kinematic data for a healthy joint model to determine which one from the list of one or more treatment plans and/or surgery plans will produce optimal results for the patient.

According to an aspect, the comparing comprises applying a pattern recognition technique on the modified 3D kinematic data, the pattern recognition technique comprising one of: a parametric or non-parametric technique, a neural network, a nearest neighbour classification technique, a projection technique, a decision tree technique, a stochastic method, a genetic algorithms and an unsupervised learning and clustering technique.

According to an aspect, the comparing further comprises classifying the modified 3D kinematic data of the joint of the patient, to which were applied the pattern recognition technique, in one of several classes of known knee joint treatment plan and/or surgery plan.

According to an aspect, the obtaining 3D kinematic data from a 3D kinematic sensor comprises obtaining 3D kinematic data from at least one of: a camera, an accelerometer, an electromagnetic sensor, a gyroscope, an optical sensor.

According to an aspect, the method further comprises:
  obtaining, from a 3D static imagery sensor, 3D static imagery data of the joint in a static position;
  merging the 3D kinematic data and the 3D static imagery data of the joint, to produce merged 3D joint data for the joint of the patient; and
  using the 3D joint data to produce and display a 3D animation of the joint.

According to an aspect, the method further comprises simulating the one or more joint treatment plans and/or surgery plans using the 3D joint data to produce a plurality of modified 3D joint data.

According to an aspect, the method further comprises comparing the plurality of modified 3D joint data to joint data for a healthy joint model to determine which one from the list of one or more treatment plans and/or surgery plans will produce optimal results for the patient.

According to an aspect, the method further comprises recalibrating the 3D joint data for a healthy joint model to adapt to measurements of the patient and thereby produce recalibrated 3D joint data for use as the 3D joint data for comparison to the plurality of modified 3D joint data.

According to an aspect, the joint comprises one of a knee, a shoulder, a wrist, an ankle, an elbow and a hip.

According to an aspect, the method further comprises installing the 3D kinematic sensor on the patient.

According to an aspect, the method further comprises storing the 3D kinematic data in memory.

According to an embodiment, there is provided a method for producing a 3D animation of a joint of patient, the 3D animation used in the determination of a list of one or more joint treatment plans and/or surgery plans for the joint of the patient, the method comprising:
    obtaining, from motion sensors, 3D kinematic data of the joint in movement;
    obtaining, from a 3D static imagery sensor, 3D static imagery data of the joint in a static position;
    merging the 3D kinematic data and the 3D static imagery data of the joint, to produce merged 3D joint data for the joint of the patient; and
    using the 3D joint data to produce and display a 3D animation of the joint.

According to an aspect, the method further comprises simulating the one or more joint treatment plans and/or surgery plans using the 3D joint data to produce a plurality of modified 3D joint data.

According to an aspect, the method further comprises comparing the plurality of modified 3D joint data to joint data for a healthy joint model to determine which one from the list of one or more joint treatment plans and/or surgery plans will produce optimal results for the patient.

According to an aspect, the method further comprises recalibrating the 3D joint data for a healthy joint model to adapt to measurements of the patient and thereby produce recalibrated 3D joint data for use as the 3D joint data for comparison to the plurality of modified 3D joint data.

According to an aspect, the recalibrating comprises performing one of a dot by dot technique and a regionalization technique.

According to an aspect, the obtaining 3D static imagery data from a static imagery sensor comprises obtaining 3D static imagery data from a radiological examination device comprising one of an X-ray machine, a Magnetic Resonance Imaging machine and a CT scanning machine.

According to an aspect, the method further comprises storing the 3D joint data for a healthy joint model in a database.

According to an embodiment, there is provided an apparatus for producing a joint treatment plan and/or surgery plan for a joint of a patient, the apparatus comprising:
    an input for receiving 3D kinematic data of the joint in movement;
    a processing device in communication with the input;
    a memory for storing instructions which cause the processing device to:
        determine, from the 3D kinematic data, scores characterising a joint function of the patient, the one or more scores being relative to one or more criteria; and
        compare the scores to data in a database which characterize a plurality of treatment plans and/or surgery plans to generate the list of one or more treatment plans and/or surgery plans which match the scores; and
    an output for outputting the list of one or more treatment plans and/or surgery plans which match the scores.

According to an embodiment, there is provided a system for producing a joint treatment plan and/or surgery plan for joint of a patient, the system comprising:
    a 3D kinematic data acquisition apparatus for obtaining 3D kinematic data of the joint in movement;
    a computing device for:
        determining, from the 3D kinematic data, scores characterising a joint function of the patient, the one or more scores being relative to one or more criteria;
        comparing the scores to data in a database which characterize a plurality of treatment plans and/or surgery plans to generate the list of one or more treatment plans and/or surgery plans which match the scores; and
        outputting the list of one or more treatment plans and/or surgery plans which match the scores.

The following terms are defined for the present disclosure.

The term "3D kinematic data" is intended to mean data representative of a combination of position, speed and acceleration of a body member such as a bone involved in a knee joint for example, irrespective of any physical force applied thereto. 3D kinematic data are obtained using motion sensors such as those employed in creating animation-type movies.

By comparison, the term "3D static imagery data" is intended to mean a data representative of a sole position. 3D static imagery data involve, for instance, the use of radiological examinations such as, without limitations, X-rays, MRI, and CT-Scans.

Even though the present disclosure provides specific examples related to knee joints, the present disclosure is meant to include other human joints such as shoulders, elbows, wrists, ankles, hips, etc.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which.

It will be noted that throughout the appended drawings, like features are identified by like reference numerals.

DETAILED DESCRIPTION

This disclosure deals with multiclass problems. These multiclass problems may dealt with using treatments such as, without limitations, arthritis-Total Knee Arthroplasty (TKA); conservative treatments such as, without limitation, physical therapy, orthotics, bracing and taping; surgical treatments or techniques such as, without limitations, implant alignment, implant type, tunnel alignment, graft type and viscosupplement (pharmacological). This leads to the knee joint treatment plan described herein.

The system which was developed will not only permit the possibility of assigning a class of treatment to a subject, but also to personalize the treatment plan and surgery. Weight bearing 3D kinematic data are used (determined by the speeds and acceleration of movement; flexion/extension curve; abduction/adduction and internal/external tibial rotation). Global and unique information for a patient is used. 3D static imagery data and 3D kinematic data as well as other pertinent 3D information are merged in order to simulate different treatments to optimize treatment planning (conservative and surgical).

This disclosure presents the following advantages: it is a treatment method that is objective and non-invasive; and it is unique in that it permits the integration of 3D biomechanical measurements (3D kinematic data) in weight bearing conditions and 3D anatomy data (3D static imagery data) from the patient as well as other 3D tools.

The method uses data such as those produced by the KneeKG™ system and performs biomechanics surgery planning (e.g., TKA, ACL reconstruction and others) by using the kinematic data co-ordinates of KneeKG™ on a rebuilt 3D model of the bones of the patient (from, for example, a Magnetic Resonance Imaging (MRI)) and by superimposing thereon a 3D model of the implant of the knee selected by the surgeon. Thanks to this tool, it is possible to determine, in simulation, if there are possibilities of reduction or loss of the range of motion of the knee. Another use of this product in surgery planning is to personalize the cut blocks and even the implants by taking into account the biomechanics of the patient.

In embodiments there are disclosed a method and an apparatus for producing a knee joint treatment plan and/or surgery plan for a patient.

Figure 1A:
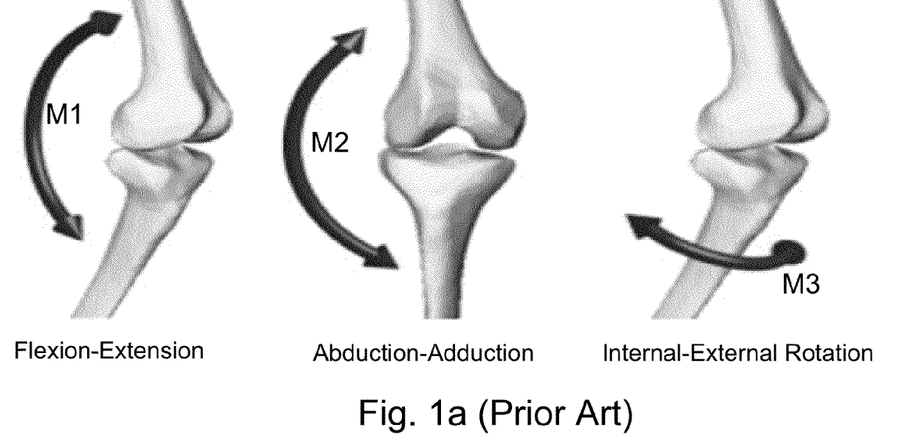
FIG. 1a is an illustration of the femur and the tibia of a knee joint, which shows three planes of motion of the knee joint, in accordance with common general knowledge associated with the prior art.
Figure 1B:
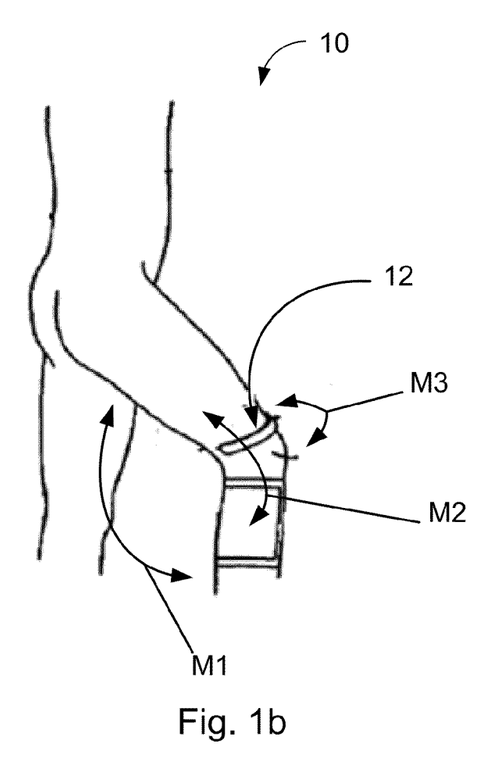
FIG. 1b is an illustration of a patient's knee joint with a sensor, and showing the three planes of motion of FIG. 1a, in accordance with an embodiment.

Referring now to the drawings and more particularly to FIG. 1b, there is shown a typical patient 10, here a human, whereby knee joint 3D kinematic data is collected using a 3D kinematic data sensor device 12, which is worn by the patient 10 over a knee joint. According to an embodiment, the 3D kinematic data is weight bearing 3D kinematic data; 3D kinematic data gathered under weight bearing conditions. The 3D kinematic data sensor device 12 is non-invasive and remains on a surface of the skin of the patient 10. It is to be noted that many types of 3D kinematic data sensor devices can be used for such purposes. Examples include optical tracking devices; electromagnetic tracking devices and accelerometers.

As seen in FIGS. 1a and 1b, a knee joint is able to move according to three different planes of motion; each of these allowing two degrees of freedom.

First plane of motion: Flexion-Extension illustrated by arrow M1: This motion refers to the capacity of movement of the knee joint to move the leg towards (flexion) the back of the thigh, and away (extension).

Second plane of motion: Abduction-Adduction illustrated by arrow M2: This motion refers to the capacity of movement of the knee joint to arc the leg towards a center axis of the body. As an example, an Abduction-Adduction plane can be apparent in a subject who as a "cowboy-like" demeanor, although this type of movement is typically subtle in most human patients.

Third plane of motion: Internal-External Rotation illustrated by arrow M3: This motion refers to the capacity of movement of the knee joint to rotate about itself (or about an axis of rotation substantially along a longitudinal plane of the leg).

The 3D kinematic data sensor device 12 monitors 3D kinematic data reflective of each of the three above described plane of motion. The 3D kinematic data gathered is thus indicative of three planes of movement (6 degrees of freedom) per knee joint of a patient.

As most knee joint disorders (be it knee osteoarthritis, anterior cruciate ligament rupture, meniscal tear, patellofemoral syndrome) have a concrete impact on knee joint movement, these can be associated to specific 3D kinematic data gathered during knee movement. Also, an abnormal knee joint movement is determined by 3D kinematic data recordings and, in some instances, is also informative for producing a knee joint treatment plan and/or surgery plan for a patient.

A database stores 3D knee joint data each associated with a given knee joint treatment and/or surgery plan for a patient. The 3D knee joint data are preloaded based on the 3D kinematic data gathered from various patients and from 3D static imagery data also gathered from various patients. For a given set of 3D knee joint data, various knee joint treatments and/or surgery plans for a patient made using a set of various means, such as imagery, expert evaluation and 3D kinematic data, are correlated with one another in order to ensure that the final knee joint treatment plan and/or surgery plan for a patient associated to the 3D knee joint data is accurate. In this way, the 3D knee joint data are each associated to a knee joint treatment and/or surgery plan for a patient.

Upon comparison of the 3D knee joint data with modified 3D knee joint data of a given patient, at least one knee joint treatment plan and/or surgery plan is determined directly and automatically and according to a quantified level of reliability, as described in greater detail below.

Figure 2:
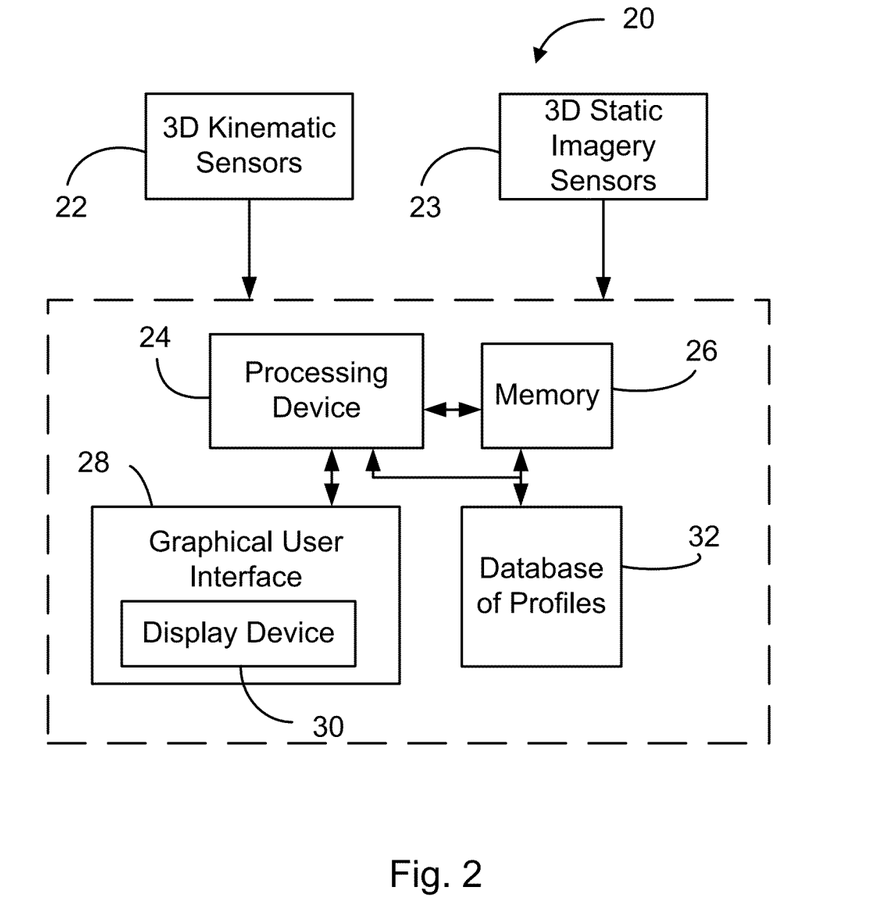
FIG. 2 is a bloc diagram of an apparatus for producing a knee joint treatment plan and/or surgery plan for a patient, in accordance with an embodiment.

FIG. 2 is a schematic illustration of an apparatus for producing a knee joint treatment plan and/or surgery plan for a patient, in accordance with an embodiment. The apparatus 20 has a set of 3D kinematic sensors 22 and 3D static imagery sensors 23 in communication with a processing device 24, a memory 26, a graphical user interface (GUI) 28, a display device 30, and a database 32.

In one embodiment, the 3D kinematic sensors 22 have tracking devices (not shown) to track position, speed and acceleration of various parts of the knee during a movement of the knee joint to generate 3D kinematic data associated to the knee joint movement as it is being performed. In this case, the 3D kinematic sensors 22 are sensing devices adapted to be attached to the patient's knee joint or other portion of the limb under evaluation. In other cases, the 3D kinematic sensors 22 are force sensors positioned so as to measure either one or a combination of 3D kinematic data and ground reaction forces during movement. Other examples of 3D kinematic sensors 22 include, but are not limited to, cameras, accelerometers and gyroscopes which are respectively positioned, for example, on the femur and the tibia of the patient. Once the 3D kinematic data are gathered from the 3D kinematic sensors 22, it is sent from the 3D kinematic sensors 22 to the processing device 24, and optionally stored to the memory.

3D static imagery data of the knee joint are also gathered in a static position from 3D static imagery sensors 23. Once the 3D static imagery data are gathered from the 3D static imagery sensors 23, it is sent from the 3D static imagery sensors 23 to the processing device 24, and optionally stored to the memory. Examples of the 3D static imagery sensors 23 may be, without limitation, the use of radiological examinations such as X-rays, MRI, and CT-Scans.

Once received at the processing device 24, either after the movement or during the time the movement is being performed, the 3D kinematic data and the 3D static imagery data are processed in the processing device 24. The processing device 24 merges the 3D kinematic data and the 3D static imagery data of the knee joint, to produce merged 3D knee joint data, in accordance with instructions stored in the memory 26. Such processing results in a 3D knee joint data of the knee joint. The 3D knee joint data is generated based on 3D kinematic data and is indicative of at least one of the three planes of motion M1, M2 and M3 of the knee joint, as discussed above in relation with FIGS. 1*a* and 1*b*. Moreover, the 3D knee joint data is generated based on the 3D static imagery data and is indicative of a static position of the knee joint.

In an embodiment, a magnetic resonance imaging (MRI) is used for reconstruction of a knee joint. For the fusion imaging to be performed (i.e., the merge of 3D kinematic data and the 3D static imagery data), axes corresponding to functional axes found in the KneeKG calibration are defined based on the healthy knee joint model, the healthy knee joint model being stored in a data library. The healthy knee joint model may then be recalibrated using a recalibrating algorithm (i.e.: a dot by dot technique) to adjust to a given patient's knee joint. A regionalization technique may also be used. The transformed (i.e., recalibrated) healthy knee joint model becomes the knee joint model used for a given patient during a surgery and/or during a treatment planning.

3D knee joint data are stored in the database 32 in association with at least one class (e.g., knee osteoarthritis, anterior cruciate ligament rupture, meniscal tear, patello-femoral syndrome) of knee joint treatment plan and/or surgery plan for a patient. A class has one or more knee joint treatment plans and/or surgery plans, which are known to be associated thereto.

Still referring to FIG. 2, the 3D knee joint data are retrieved from database 32 by the processing device 24. The processing device 24 then proceeds by applying a pattern recognition technique on these 3D knee joint data, from which a classification of the 3D knee joint data of the knee joint under analysis is made by processing device 24.

The pattern recognition and the classification are performed in the processing device 24. Various types of pattern recognition (also referred to pattern classification) techniques can be used, as per instructions (also referred to as coding) stored in the memory 26. For example, any computer implemented pattern recognition technique between the 3D knee joint data and a knee joint treatment and/or surgery plan is used, such as, for example, any type of machine learning techniques to provide an automated machine classification and decision-making based on the 3D knee joint data.

A non-exhaustive list of possible implementations used for pattern recognition includes: a parametric or non-parametric technique, a neural network, a nearest neighbour classification technique, a projection technique, a decision tree technique, a stochastic method, a genetic algorithms and an unsupervised learning and clustering technique.

The processing device 24 proceeds to classify the 3D knee joint data of the knee joint into one of several classes of known knee joint treatment plan and/or surgery plan for a patient, based on the results from the pattern recognition technique.

Once the classification of the 3D knee joint data is done, a knee joint treatment plan and/or a surgery plan for a patient is identified based on the class(es) in which the 3D knee joint data has been classified, and the identified knee joint treatment plan and/or surgery plan for a patient is outputted by the processing device 24.

More particularly, the knee joint treatment plan and/or surgery plan for a patient identified corresponds to the knee joint plan in the class of knee joint plans under which the 3D knee joint data has been classified by the processing device 24. For example, if the 3D knee joint data is classified in a class of knee joint treatment plan and/or surgery plan associated to a meniscus tear, then the identified plan corresponds or at least comprises a knee joint treatment plan or a surgery plan for the meniscus tear.

In some instances, the plan identified can in fact combine more than one knee joint treatment plan and/or surgery plan when the 3D knee joint data is classified in a class associate to more than one plan.

In addition, the database 32 can store the 3D knee joint data for the knee joint of different patients, any type of patient-identification data, and the 3D kinematic data and 3D static imagery data received from the 3D kinematic sensors 22 and 3D static imagery sensors 23. In one embodiment, the database 32 stores a plurality of sets of 3D knee joint data; each set being associated to a particular class of plans (knee joint treatment plan and/or surgery plan for a patient).

The GUI 28 and the display device 30 are in communication with one another and with the processing device 24 (and in one embodiment, with the memory 26). The GUI 28 receives either one or a combination of the classification for the knee joint under analysis and the identified plan, whichever appropriate in a specific class. In either case, however, the GUI 28 displays either one or a combination of the classification and the particular plan identified, including a description of the knee joint treatment plan and/or surgery plan involved, on the display device 30. The GUI 28 may also display the 3D knee joint problem generated from the 3D kinematic data and the 3D static imagery data.

The GUI 28 allows user interaction such that a particular display setting is activated on the display device 30, to show either or a combination of: the 3D knee joint data, the knee joint treatment plan and/or the surgery plan relevant to the 3D knee joint data identified, in accordance with a user preference.

Still in reference to FIG. 2, it is noted that in one embodiment, the kinematic sensors 22 are embodied as a commonly available 3D knee movement analyser such as the one described in U.S. Pat. No. 7,291,119, and having a set of tracking sensors suited to obtain 3D kinematic data for tibio-femoral movements of a knee joint. The 3D kinematic sensors 22 can however be of any type of dynamic 1 D, 2D or 3D knee analyzer based on either one or a combination of available technologies such as provide for the monitical, electromagnetic, accelerometers, which provide for the monitoring of an acceleration, position and speed.

Figure 3:
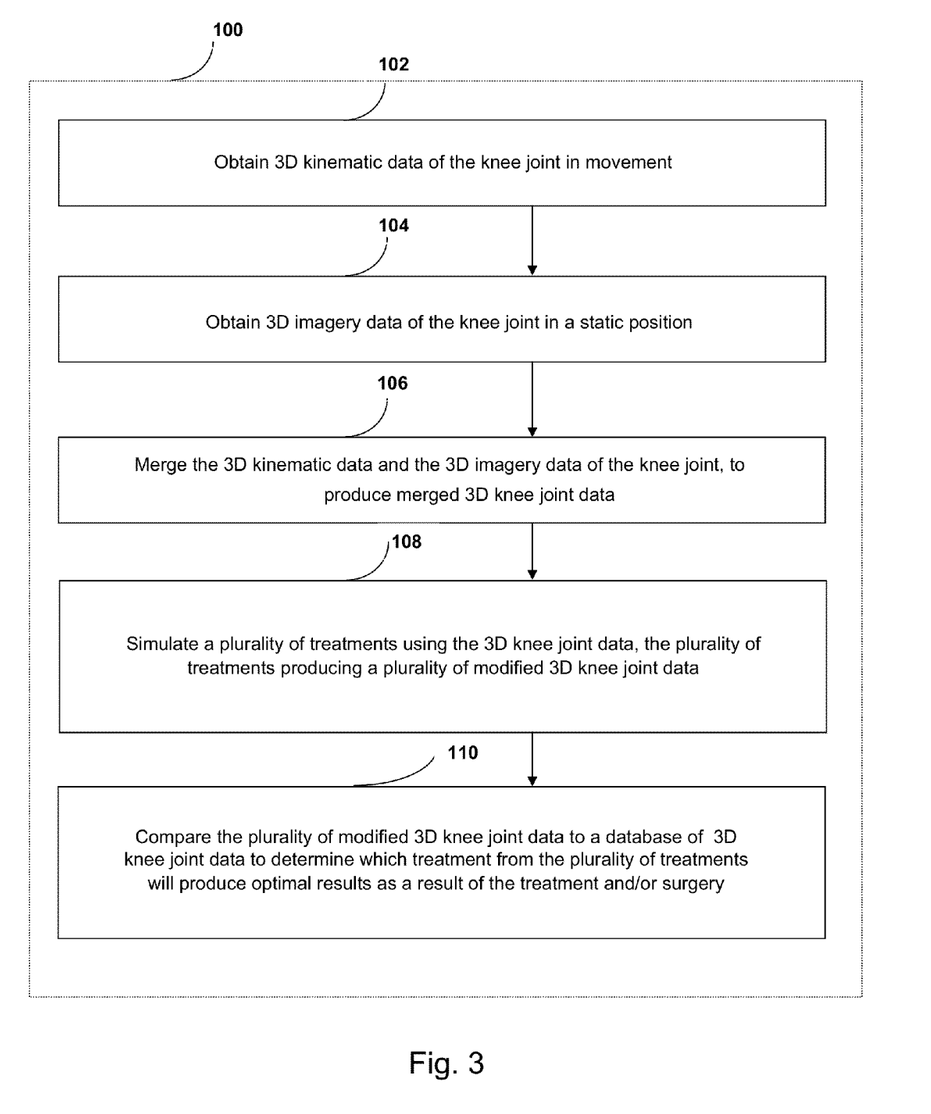
FIG. 3 is a flow chart of a method for producing a knee joint treatment plan and/or surgery plan for a patient, in accordance with an embodiment.

In addition to the above-noted apparatus 20, it is noted that in one embodiment, the apparatus 20 is adapted to perform any of the below-detailed steps of a method 100 for producing a knee joint treatment plan and/or surgery plan for a patient, described in relation to FIG. 3. The method 100 comprises the step 102 of obtaining 3D kinematic data of the knee joint in movement. The 3D kinematic data is representative of a movement performed by a knee joint, in accordance with one of the three planes of movement defined above in reference to FIGS. 1a and 1b. The method 100 further comprises the step 104 of obtaining 3D static imagery data of the knee joint in a static position. According to another embodiment, step 104 is replaced by obtaining 3D dynamic imagery data such as from a dynamic MRI or from Radiostereometric Analysis (RSA). Moreover, the method 100 comprises the step 106 of merging the 3D kinematic data and the 3D static imagery data of the knee joint, to produce merged 3D knee joint data. The method 100 further comprises the step 108 of simulating a plurality of treatments using the 3D knee joint data, when the plurality of treatments produces a plurality of modified 3D knee joint data. Furthermore, the method 100 comprises the step 110 of comparing the plurality of modified 3D knee joint data to a database of 3D knee joint data to determine which treatment from the plurality of treatments will produce optimal results as a result of the treatment and/or surgery.

The identification of such knee joint treatments is performed by a computer device in accordance to this method 100 and thereby provides assistance in medical treatments and surgeries.

In an embodiment, the knee joint treatments are archived for further analysis, reporting or display on an output of any type, such as email or other network-based notification addressed to authenticated users for example.

In an embodiment, the method 100 also optionally involves displaying the 3D knee joint data and/or the knee joint treatment plan and/or surgical plan for a patient in accordance with a given format. The format can be as per a user entered preference(s) or set by default. In one embodiment, the displaying optionally involves generating a set of graphical illustrations to represent the data according to at least one of the three planes of motion as they are sensed by the motion sensor during the movement. In one embodiment, the planes of motion are provided in terms of degrees, and the time elapsed during the movement of the knee joint is provided in terms of percentage of the movement performed.

Figure 4:
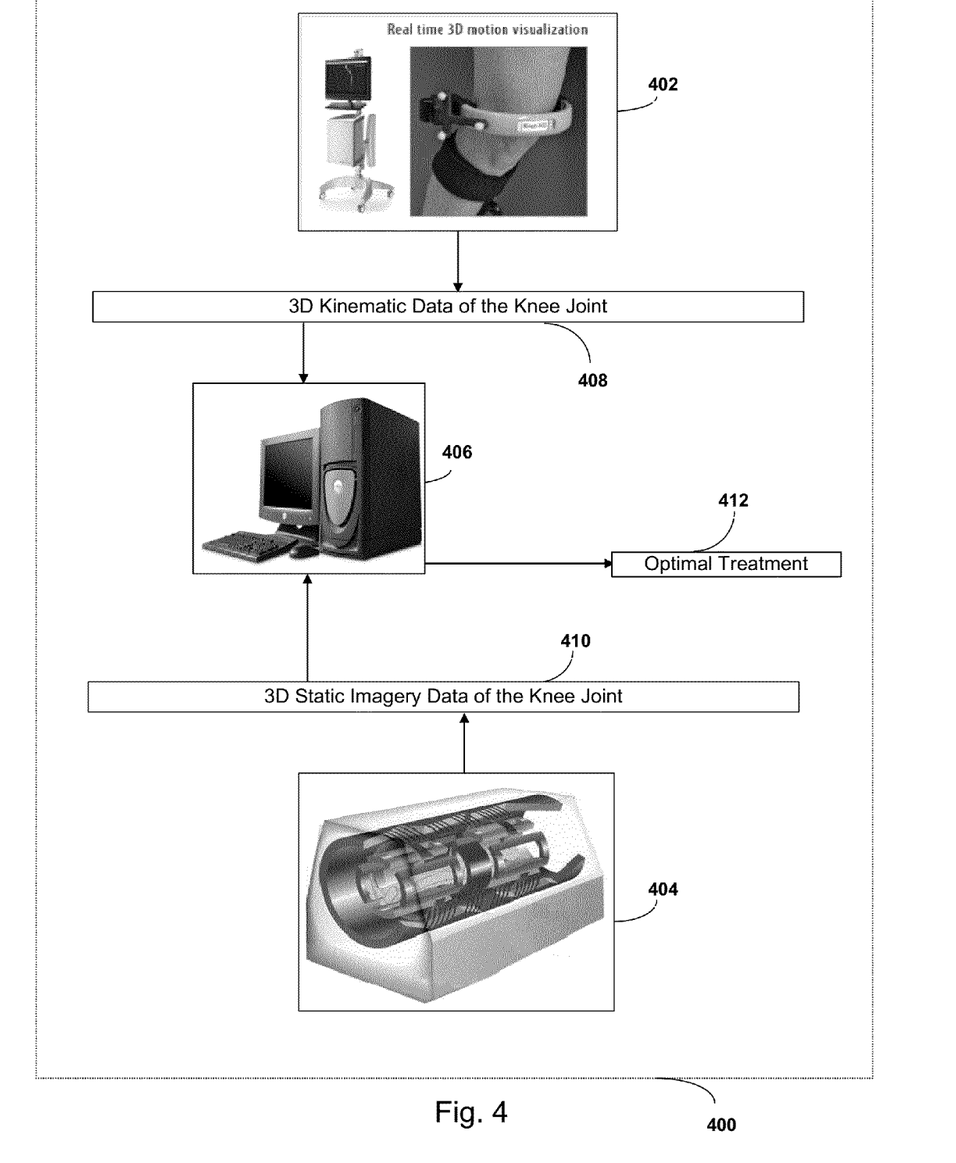
FIG. 4 is a schematic illustration of the system for producing a knee joint treatment plan and/or surgery plan for a patient, in accordance with an embodiment.

Now referring to FIG. 4, there is shown a schematic illustration of a system 400 for producing a knee joint treatment plan and/or surgery plan for a patient, in accordance with an embodiment. The system 400 comprises 3D knee kinematic data acquisition apparatus 402, a 3D knee static imagery data acquisition apparatus 404 (such as X-rays, MRI, and CT-Scans) and a computing device 406. The 3D knee kinematic data acquisition apparatus 402 obtains the 3D knee kinematic data 408. The 3D knee static imagery data acquisition apparatus 404 obtains the 3D knee static imagery data 410. Both the 3D knee kinematic data 408 and the 3D knee static imagery data 410 are fed to the computing device 406 which merges them to produce 3D knee joint data and simulates a plurality of treatments using the 3D knee joint data to finally determine which treatment from the plurality of treatments will produce optimal results 412 as a result of the treatment and/or surgery.

Figure 5:
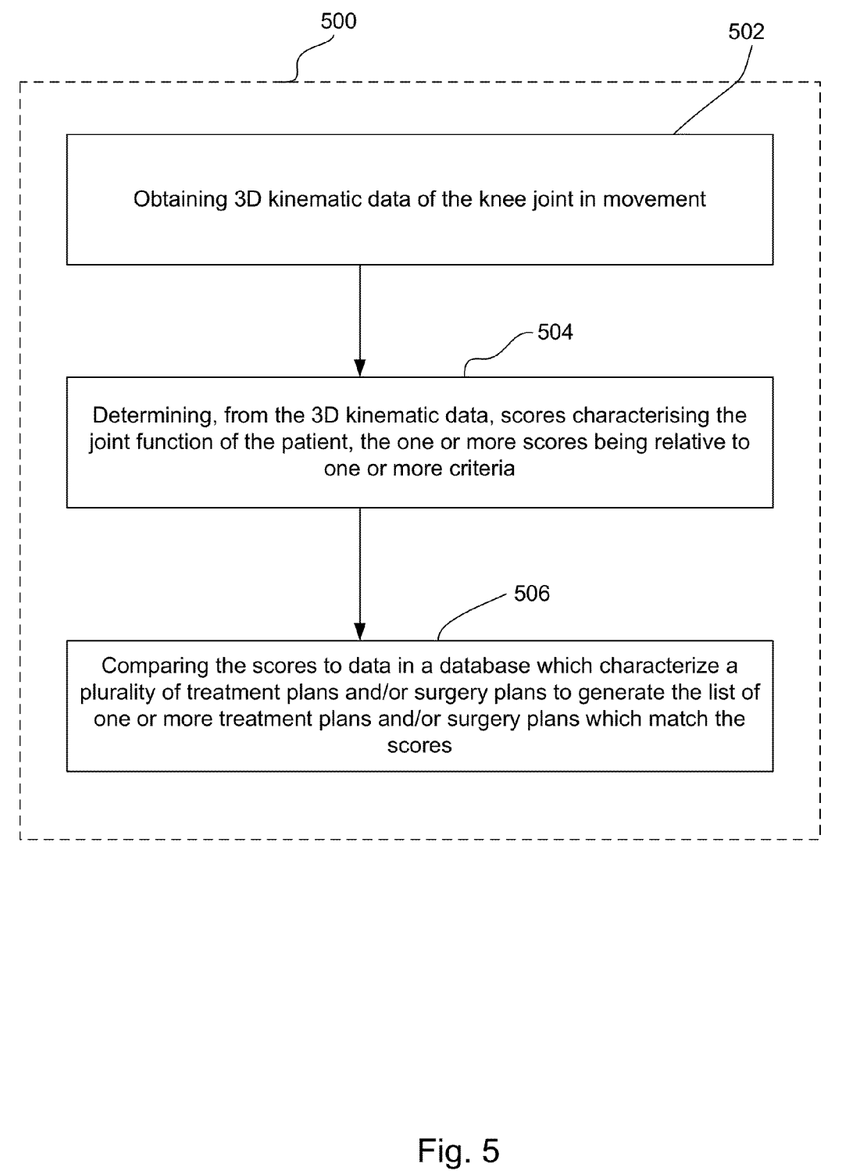
FIG. 5 is a flow chart of a method for producing a knee joint treatment plan and/or surgery plan for a patient, in accordance with another embodiment.

Now referring to FIG. 5, there is shown a flow chart of a method 500 for producing a knee joint treatment plan and/or surgery plan for a patient, in accordance with an embodiment. The method 500 for producing a knee joint treatment plan and/or surgery plan for a patient may comprise the step 502 of obtaining, from motion sensors, 3D kinematic data of the knee joint in movement, the step 504 of determining, from the 3D kinematic data, scores characterising the joint function of the patient, the one or more scores being relative to one or more criteria; and the step 506 of comparing the scores to data in a database which characterize a plurality of treatment plans and/or surgery plans to generate the list of one or more treatment plans and/or surgery plans which match the scores.

In an embodiment, the criteria; for the scores include, but are not limited to, varus thrust, flexum, fixed flexion, and dynamic vargus. The table shows an exemplary case study in a conservative mode treatment for different scores characterizing the joint functions of a patient.

| Criteria | Score (degrees) | Treatment/surgery plan |
| --- | --- | --- |
| Flexum at heel strike | 11.3 | Stretching of the hamstrings and calf muscles; strengthening of the quadriceps muscles (working the quadriceps in the last degrees of knee extension); make the heel strike with full extension to diminish pressure between the femora and patella) |
| External Tibial Rotation at heel strike | 8.5 | Stretching of the tensor fasciae latae and the biceps femoris muscles |
| Internal tibial rotation movement | 5.3 | Physiotherapy: assess muscles deficits associated with internal femoral rotation during the loading phase loading phase, assess hip abductors muscles, assess the pertinence of proprioceptive knee taping |

Figure 6:
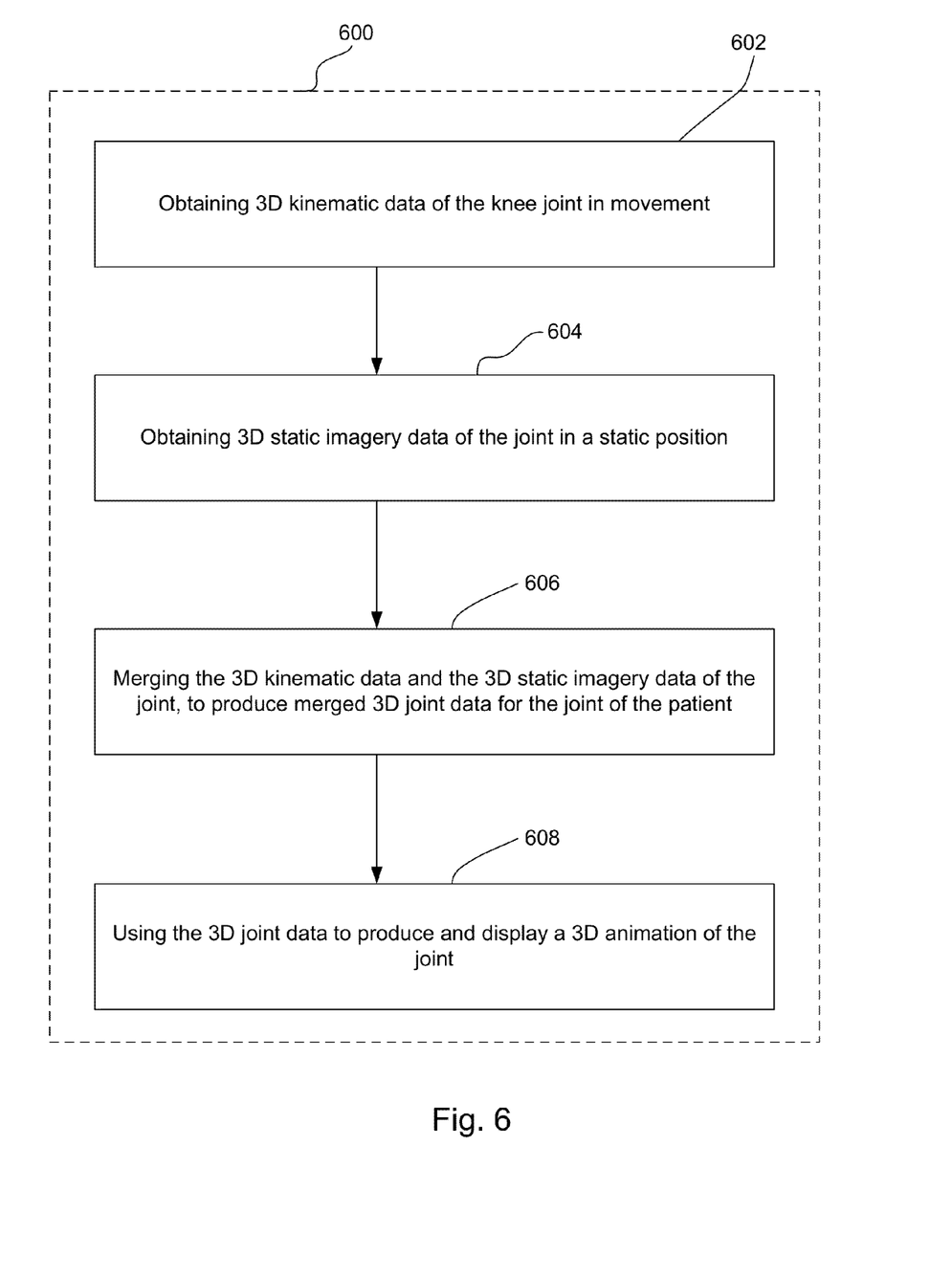
FIG. 6 is a flow chart of a method for producing a 3D animation of a joint of patient, in accordance with an embodiment.

Now referring to FIG. 6, there is shown an embodiment of a method 600 for producing a 3D animation of a joint of patient. The 3D animation is used to help the physician in the determination of a list of one or more joint treatment plans and/or surgery plans for the joint of the patient and in the selection of the best joint treatment plans and/or surgery plans for the patient's condition. The method comprises: obtaining, from motion sensors, 3D kinematic data of the joint in movement (step 602); obtaining, from a 3D static imagery sensor, 3D static imagery data of the joint in a static position (step 604); merging the 3D kinematic data and the 3D static imagery data of the joint, to produce merged 3D joint data for the joint of the patient (step 606); and using the 3D joint data to produce and display a 3D animation of the joint (step 608). According to another embodiment, step 604 is replaced by obtaining 3D dynamic imagery data such as from a dynamic MRI or from Radiostereometric Analysis (RSA).

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A method for generating a list of one or more joint treatment plans and/or surgery plans for a joint of a patient, the method comprising:
   obtaining, from motion sensors, 3D kinematic data of the joint in movement;
   determining, from the 3D kinematic data, scores characterising a joint function of the patient, the scores being relative to one or more criteria; and
   comparing the scores to data in a database which characterize a plurality of treatment plans and/or surgery plans to generate the list of one or more joint treatment plans and/or surgery plans which match the scores.

2. The method of claim 1, further comprising simulating the one or more joint treatment plans and/or surgery plans using the 3D kinematic data to produce a plurality of modified 3D kinematic data.

3. The method of claim 2, further comprising comparing the plurality of modified 3D kinematic data to kinematic data for a healthy joint model to determine which one from the list of one or more treatment plans and/or surgery plans will produce optimal results for the patient.

4. The method of claim 3, wherein the comparing comprises applying a pattern recognition technique on the modified 3D kinematic data, the pattern recognition technique comprising one of: a parametric or non-parametric technique, a neural network, a nearest neighbour classification technique, a projection technique, a decision tree technique, a stochastic method, a genetic algorithms and an unsupervised learning and clustering technique.

5. The method of claim 4, wherein the comparing further comprises classifying the modified 3D kinematic data of the joint of the patient, to which were applied the pattern recognition technique, in one of several classes of known knee joint treatment plan and/or surgery plan.

6. The method of claim 1, wherein the obtaining 3D kinematic data from a 3D kinematic sensor comprises obtaining 3D kinematic data from at least one of: a camera, an accelerometer, an electromagnetic sensor, a gyroscope, an optical sensor.

7. The method of claim 1, further comprising:
obtaining, from a 3D static imagery sensor, 3D static imagery data of the joint in a static position;
merging the 3D kinematic data and the 3D static imagery data of the joint, to produce merged 3D joint data for the joint of the patient; and
using the 3D joint data to produce and display a 3D animation of the joint.

8. The method of claim 7, further comprising simulating the one or more joint treatment plans and/or surgery plans using the 3D joint data to produce a plurality of modified 3D joint data.

9. The method of claim 8, further comprising comparing the plurality of modified 3D joint data to joint data for a healthy joint model to determine which one from the list of one or more joint treatment plans and/or surgery plans will produce optimal results for the patient.

10. The method of claim 9, further comprising recalibrating the 3D joint data for a healthy joint model to adapt to measurements of the patient and thereby produce recalibrated 3D joint data for use as the 3D joint data for comparison to the plurality of modified 3D joint data.

11. The method of claim 1, further comprising storing the 3D kinematic data in memory.

12. The method of claim 1, wherein the criteria at least comprise varus thrust, flexum, fixed flexion, and dynamic vargus.

13. A computer-implemented method for producing a 3D animation of a joint of patient, the 3D animation used in the determination of a list of one or more joint treatment plans and/or surgery plans for the joint of the patient, the method comprising:
at an input device:
obtaining, from motion sensors, 3D kinematic data of the joint in movement; and
obtaining, from a 3D static imagery sensor, 3D static imagery data of the joint in a static position; and
at a processing device in communication with the input device:
merging the 3D kinematic data and the 3D static imagery data of the joint, to produce merged 3D joint data for the joint of the patient;
using the 3D joint data to produce and display a 3D animation of the joint; and
generating the list of one or more joint treatment plans and/or surgery plans for the joint of the patient.

14. The method of claim 13, further comprising simulating the one or more joint treatment plans and/or surgery plans using the 3D joint data to produce a plurality of modified 3D joint data.

15. The method of claim 14, further comprising comparing the plurality of modified 3D joint data to joint data for a healthy joint model to determine which one from the list of one or more joint treatment plans and/or surgery plans will produce optimal results for the patient.

16. The method of claim 15, further comprising recalibrating the 3D joint data for a healthy joint model to adapt to measurements of the patient and thereby produce recalibrated 3D joint data for use as the 3D joint data for comparison to the plurality of modified 3D joint data.

17. The method of claim 16, wherein the recalibrating comprises performing one of a dot by dot technique and a regionalization technique.

18. The method of claim 13, wherein the obtaining 3D static imagery data from a static imagery sensor comprises obtaining 3D static imagery data from a radiological examination device comprising one of an X-ray machine, a Magnetic Resonance Imaging machine and a CT scanning machine.

19. The method of claim 13, further comprising storing the 3D joint data for a healthy joint model in a database.

20. An apparatus for generating a list of one or more joint treatment plan and/or surgery plan for a joint of a patient, the apparatus comprising:
an input for receiving 3D kinematic data of the joint in movement;
a processing device in communication with the input;
a memory for storing instructions which cause the processing device to:
determine, from the 3D kinematic data, scores characterising a joint function of the patient, the one or more scores being relative to one or more criteria; and
compare the scores to data in a database which characterize a plurality of treatment plans and/or surgery plans to generate the list of one or more joint treatment plans and/or surgery plans which match the scores; and
an output for outputting the list of one or more joint treatment plans and/or surgery plans which match the scores.

* * * * *